(12) United States Patent
Feldman

(10) Patent No.: US 7,347,466 B1
(45) Date of Patent: Mar. 25, 2008

(54) MULTIPURPOSE CONTACT LENS ACCESSORY

(76) Inventor: Michael Alan Feldman, 19 Reunion Rd., Rye Brook, NY (US) 10573

( * ) Notice: Subject to any disclaimer, the term of this patent is extended or adjusted under 35 U.S.C. 154(b) by 0 days.

(21) Appl. No.: 11/057,362

(22) Filed: Feb. 14, 2005

(51) Int. Cl.
A61F 9/00 (2006.01)

(52) U.S. Cl. .............. 294/1.2; 623/6.11; 623/6.12; 351/160 R; 606/107; 206/5.1

(58) Field of Classification Search .......... 623/6.11, 623/6.12; 351/160 R; 294/1.2
See application file for complete search history.

(56) References Cited

U.S. PATENT DOCUMENTS

| | | | | |
|---|---|---|---|---|
| 3,304,113 A | * | 2/1967 | Hutchison | 294/1.2 |
| 3,344,461 A | * | 10/1967 | Floor | 15/118 |
| 3,934,914 A | * | 1/1976 | Carruthers | 294/1.2 |
| 4,082,339 A | * | 4/1978 | Ross | 294/1.2 |
| 4,286,815 A | * | 9/1981 | Clark | 294/1.2 |
| 4,385,810 A | * | 5/1983 | Hamou | 359/381 |
| 4,452,514 A | * | 6/1984 | Spitznas | 351/206 |
| 4,512,602 A | * | 4/1985 | England | 294/1.2 |
| 4,784,258 A | * | 11/1988 | Figari | 206/5.1 |
| 5,099,987 A | * | 3/1992 | Bieri | 206/5.1 |
| 5,246,259 A | * | 9/1993 | Hellenkamp et al. | 294/1.2 |
| 5,688,007 A | * | 11/1997 | Jefferson | 294/1.2 |
| 5,688,224 A | * | 11/1997 | Forkey et al. | 600/200 |
| 5,788,706 A | * | 8/1998 | Deminski | 606/107 |
| 6,092,646 A | * | 7/2000 | Glazier | 206/5.1 |
| 6,365,111 B1 | * | 4/2002 | Bass | 422/102 |
| 6,401,915 B1 | * | 6/2002 | Faxe | 206/5.1 |
| 2002/0009217 A1 | * | 1/2002 | Bickert et al. | 382/141 |
| 2005/0194798 A1 | * | 9/2005 | Wallock et al. | 294/1.2 |

* cited by examiner

Primary Examiner—Linda C. M. Dvorak
Assistant Examiner—Matthew J. Kasztejna
(74) Attorney, Agent, or Firm—Kajane McManus

(57) ABSTRACT

The multipurpose contact lens accessory comprises a casing having a contact end and a viewing end, the viewing end having a lens therein, wherein the contact end engages a contact thereon for viewing and/or insertion of same and the viewing end allows for viewing of the contact engaged to the contact end for determining if any visible defects exist in the contact and/or whether the contact is inside out.

6 Claims, 2 Drawing Sheets

MULTIPURPOSE CONTACT LENS ACCESSORY

BACKGROUND OF THE INVENTION

1. Field of the Invention

The present invention relates to a multipurpose contact lens accessory.

More specifically, the accessory is used for easing insertion of a contact lens, for checking a lens for visible defects therein, and for making sure a lens is not inserted inside out.

2. Prior Art

Heretofore, various lens insertion devices have been proposed. However, none have been adapted for multipurpose use as described above.

SUMMARY OF THE INVENTION

According to the invention there is provided a multipurpose contact lens accessory comprising a casing having a contact end and a viewing end, the viewing end having a lens therein wherein the contact end engages a contact thereon for viewing or insertion of same and the viewing end allows for viewing of the contact engaged to the contact end for determining if any visible defects exist in the contact and/or whether the contact is inside out.

DESCRIPTION OF THE PREFERRED EMBODIMENTS

Figure 1:
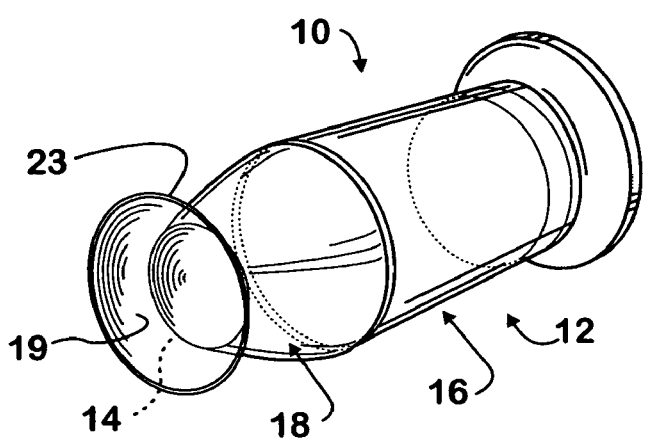
FIG. 1 is a perspective view of the accessory of the present invention.
Figure 2:
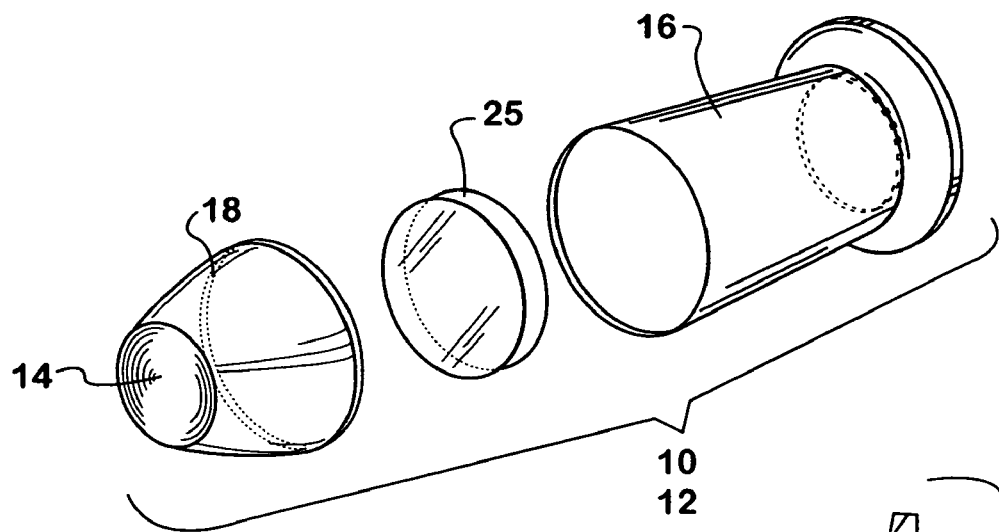
FIG. 2 is a perspective exploded view of the accessory of FIG. 1.

Referring now to the drawings in greater detail there is illustrated therein the multipurpose contact lens accessory made in accordance with the teachings of the present invention and generally identified by the reference numeral 10.

Figure 3:
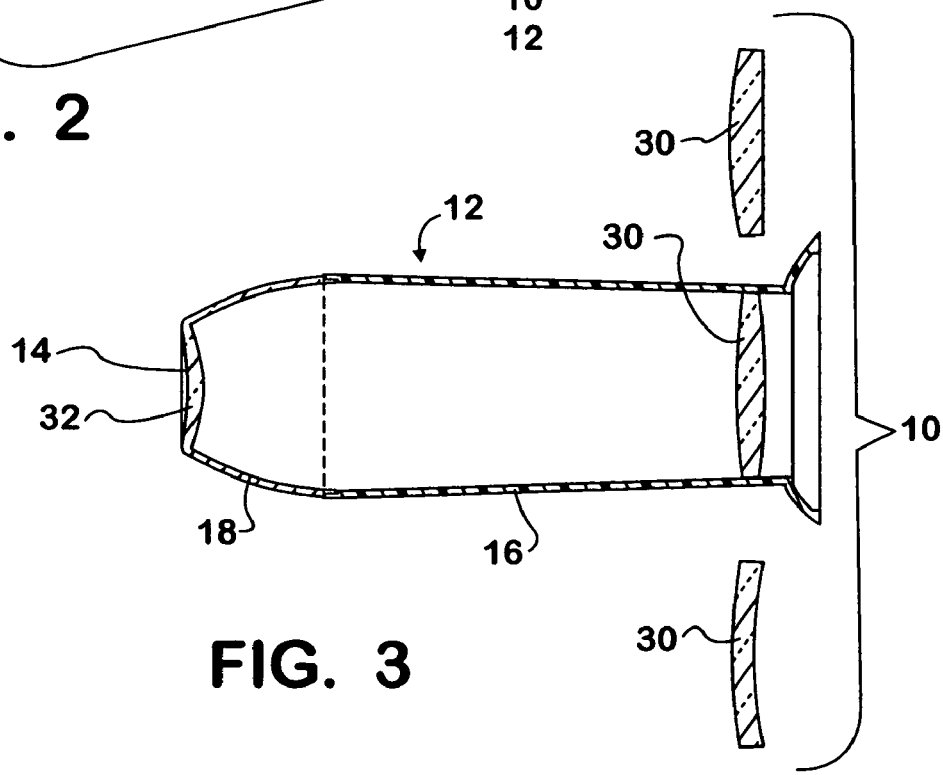
FIG. 3 is a cross sectional view of the accessory showing useable configurations of lenses for the viewing end of the accessory.

As shown, the accessory 10, in a preferred embodiment, is comprised of a two piece casing 12 having a concavoconvex lens 14 therein. The casing 12 comprises an eyepiece or viewing end 16 and a contact end 18, and the lens 14, if desired, can be formed as part of contact end 18. Provision of the lens 14 allows for higher magnification viewing of a contact lens 19 engaged by capillary action to a concave contact well 14 formed by lens 14 at contact end 18 by looking into eyepiece end 16, as shown in FIG. 3. Alternatively, no lens is required on the contact end 18. Thus, it will be understood that the accessory 10 is a "view through" device.

Such "view through" allows a user to inspect a hard or soft contact 19 engaged within the well 14 under high magnification to check the contact 19 for visible defects. Further, in the case of a soft contact 19, a user can determine whether the lens 19 is inside out or not, prior to inserting same. In this respect, a lens manufacturer's logo, code, or number is typically printed along an area on an edge of an outer surface 23 of the lens. Thus, if the logo is viewed from viewing end 16 of the accessory 10 appears backward, the user knows the contact 19 is inside out and must be flipped.

Figure 4:
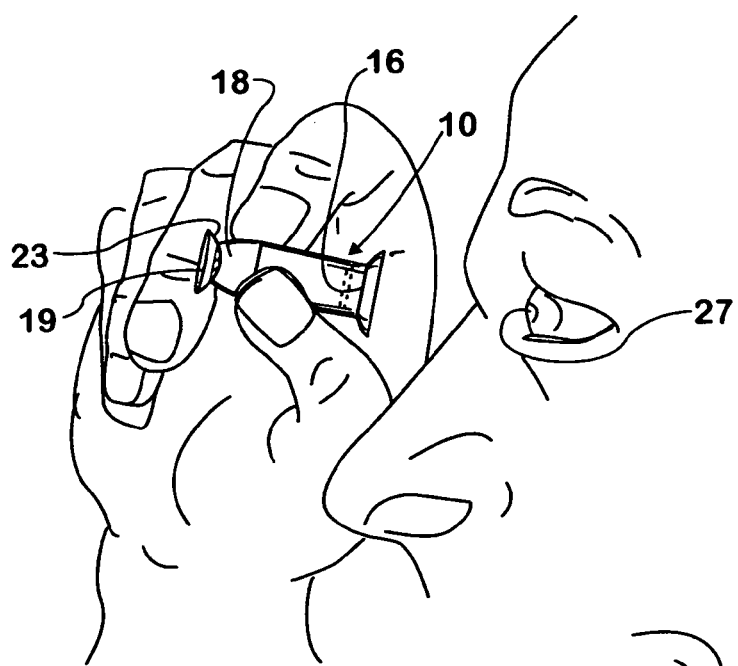
FIG. 4 is a perspective view showing the accessory in use for examining a lens.
Figure 5:
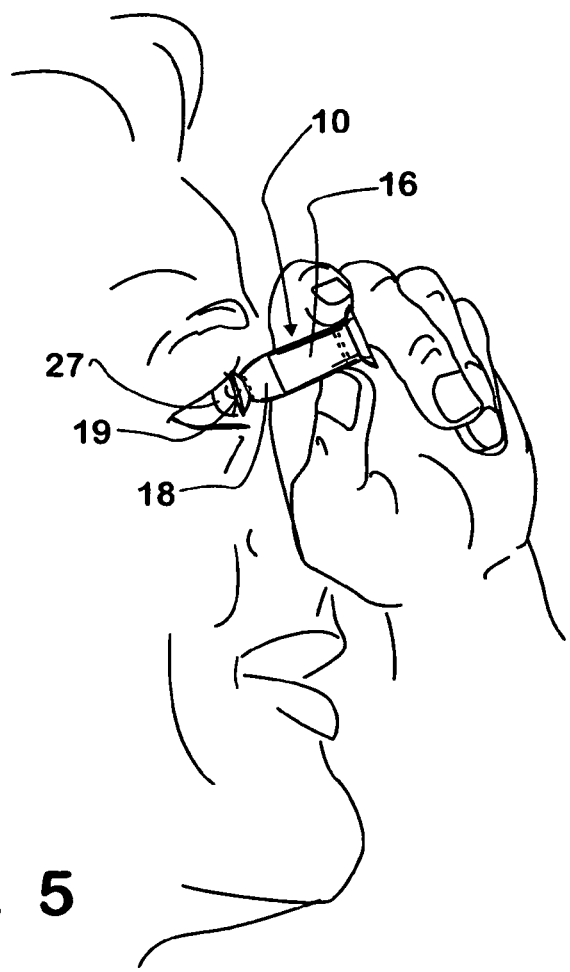
FIG. 5 is a perspective view of the accessory in use for inserting a lens.

If the logo appears appropriately and no visible defect is detected, the user merely turns the well 14 toward his eye and inserts the contact 19 by touching same to the eyeball 27 as shown in FIG. 4.

In a preferred embodiment, which should not be construed as limiting, contact end 18 is preferably made of a clear acrylic material and can have the concavoconvex lens 14 inserted into it with a focal length that allows the contact 19 placed on contact end 18 to be in focus. The concavoconvex lens 14 can also be "molded" into and along with contact end 18. Contact end 18 can be made from any one of a number of clear acrylic polymers or "softer" water clear elastomers.

The viewing end 16 incorporates a lens 30 therein which, in the preferred embodiment, is bi-convex relative to the eye of the user and has a focal length or working distance to allow viewing of the contact with higher magnification. The lens 30 can be of another embodiment, such as planoconvex, concavoconvex, etc, as illustrated in FIG. 3. Thus, the configuration thereof should not be construed at limiting. The viewing end 16 can be made of any clear, translucent or opaque acrylic polymer.

The lens 14 at the contact end 18, on the other hand, is created with a concavoconvex configuration, as illustrated, with the concave surface 32 facing outwardly of the accessory 10 upon which the contact 19 is perched, to allow for viewing of a logo (not shown) on the contact 19, as well as allowing for examination of the contact 19 to look for any visible defects therein.

The two casing 12 pieces 16, 18 are snapped together for a water tight fit. The device may have a hollow air filled interior or may be filled with a liquid or may be solid which would require different optics due to a different index of refraction of either medium, as is known.

In a preferred embodiment, the viewing end 16 is translucent and the contact end 18 is clear, though this should not be construed as limiting.

In use, a contact 19 is engaged to the contact end 18 and is maintained there by capillary action.

One then examines the contact 19 by looking through the viewing end 16 for rips or other visible defects therein.

Also, one examines the contact 19 for visualization of a manufacturer's marking thereon. If the marking is reversed, the contact 19 is inside out and must be flipped.

If the marking appears correctly, the accessory 10 is reversed so contact end 18 faces the user, and used to easily apply the contact 19 to the eyeball 27.

As described above, the accessory 10 of the present invention, in combination with the method of creating the device 10, provides a number of advantages, some of which have been described above and others of which are inherent in the invention. Also, modifications to the device 10 and method of creating same can be proposed without departing from the teachings herein. Accordingly, the scope of the invention is only to be limited as necessitated by the accompanying claims.

The invention claimed is:

1. A contact viewing and insertion accessory comprising a unitary casing having a contact lens engaging end and an opposite viewing end, the viewing end having a lens therein, wherein the contact lens engaging end engages a contact lens thereon by capillary action for viewing, from the viewing end, and/or insertion of the contact lens and the viewing end allows for viewing of the contact lens engaged to the contact lens engaging end, from the viewing end through the accessory, prior to insertion of the contact lens, for determining if any visible defects exist in the contact lens and/or whether the contact lens is inside out.

2. The accessory of claim 1 wherein viewing end of the casing is translucent, clear or opaque.

3. The accessory of claim 1 wherein the contact lens engaging end of the casing is transparent.

4. The accessory of claim 1 wherein the contact lens engaging end incorporates a lens.

5. The accessory of claim 1 wherein a lens at the contact lens engaging end of the casing is concavoconvex when viewed from the contact lens engaging end.

6. The accessory of claim 1 wherein the lens at the viewing end is one taken from the group comprising: biconvex, planoconvex, and concavoconvex when viewed from the viewing end.

* * * * *